US012245890B2

(12) United States Patent
Sethuraman et al.

(10) Patent No.: US 12,245,890 B2
(45) Date of Patent: Mar. 11, 2025

(54) APPARATUSES, SYSTEMS AND METHODS FOR PROVIDING ACQUISITION FEEDBACK

(71) Applicant: KONINKLIJKE PHILIPS N.V., Eindhoven (NL)

(72) Inventors: Shriram Sethuraman, Lexington, MA (US); Sibo Li, Waltham, MA (US); William Tao Shi, Wakefield, MA (US); James Robertson Jago, Seattle, WA (US); Thanasis Loupas, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 34 days.

(21) Appl. No.: 18/276,462

(22) PCT Filed: Jan. 29, 2022

(86) PCT No.: PCT/EP2022/052155
§ 371 (c)(1),
(2) Date: Aug. 9, 2023

(87) PCT Pub. No.: WO2022/171465
PCT Pub. Date: Aug. 18, 2022

(65) Prior Publication Data
US 2024/0164756 A1    May 23, 2024

Related U.S. Application Data

(60) Provisional application No. 63/148,224, filed on Feb. 11, 2021.

(51) Int. Cl.
*A61B 8/00* (2006.01)
*A61B 8/06* (2006.01)

(52) U.S. Cl.
CPC .............. *A61B 8/469* (2013.01); *A61B 8/06* (2013.01); *A61B 8/465* (2013.01); *A61B 8/488* (2013.01); *A61B 8/5276* (2013.01)

(58) Field of Classification Search
CPC .......... A61B 8/06; A61B 8/465; A61B 8/469; A61B 8/483; A61B 8/488; A61B 8/52; A61B 8/5276
See application file for complete search history.

(56) References Cited

U.S. PATENT DOCUMENTS 6,086,539 A    7/2000  Guracar et al.
6,443,896 B1   9/2002  Detmer
(Continued)

FOREIGN PATENT DOCUMENTS

WO    2018215641 A1    11/2018

OTHER PUBLICATIONS

International Search Report and Written Opinion for PCT/EP2022/052155; Mailing date: Apr. 12, 2022, 9 pages.
(Continued)

*Primary Examiner* — Boniface N Nganga

(57) ABSTRACT

User feedback on acquisition of ultrasound data may be provided to a user. The feedback may indicate a quality of the acquisition and/or the reliability of the measurements calculated from the ultrasound data, for example, the volume flow measurements calculated from Doppler data. Various quality factors such as a signal-to-noise ratio (SNR), motion, Doppler angle, vessel size, vessel depth, and/or variance in velocity values may be determined to provide an indication of quality of the acquisition. The quality factors may be provided individually or in combination. In some examples, one or more quantitative values of the quality factors may be provided. In some examples, one or more qualitative indications of the quality of the acquisition may be provided.

20 Claims, 6 Drawing Sheets

(56) References Cited

U.S. PATENT DOCUMENTS

| | | |
|---|---|---|
| 6,530,885 B1 | 3/2003 | Entrekin et al. |
| 6,535,835 B1 | 3/2003 | Rubin et al. |
| 6,780,155 B2 | 8/2004 | Li |

OTHER PUBLICATIONS

Kripfgans, O. et al., "Partial Volume Effect and Correction for 3-D Color Flow Acquisition of Volumetric Blood Flow," in IEEE Transactions on Ultrasonics, Ferroelectrics, and Frequency Control, 2019, vol. 66, No. 11, pp. 1749-1759.

Kripfgans, O. et al., "Measurement of Volumetric Flow", Journal of Ultrasound in Medicine, 2006, vol. 25, Issue 10, pp. 1305-1311.

APPARATUSES, SYSTEMS AND METHODS FOR PROVIDING ACQUISITION FEEDBACK

CROSS-REFERENCE TO PRIOR APPLICATIONS

This application is the U.S. National Phase application under 35 U.S.C. § 371 of International Application No. PCT/EP2022/052155, filed on Jan. 29, 2022, which claims the benefit U.S. Provisional Patent Application No. 63/148,224, filed on Feb. 11, 2021. These applications are hereby incorporated by reference herein.

TECHNICAL FIELD

This application relates to providing acquisition feedback. More specifically, this application relates to providing feedback on acquired ultrasound data.

BACKGROUND

Ultrasound Doppler imaging is typically used in a qualitative manner to determine the presence or absence of flow. A more quantitative measure such as blood velocities can be estimated from Doppler shifts occurring in a sample volume after correction for the Doppler angle in modes such as spectral Doppler. While velocities are an important measure, total flow is a measure that may better represent the well-being of an organ or body. Current methods for estimation of blood volume flow through a blood vessel implemented on several clinical ultrasound systems are based on one dimensional (1D) spectral Doppler. Estimation of blood volume flow entails steps that are operator dependent such as determination of the diameter of the vessel based on cursors placed by the operator on the B-Mode image and a sample volume from which the velocity is estimated is also selected by the operator. Additionally, the angle of the probe relative to the volume is based on how the operator holds the probe. Typically, spectral Doppler requires angle correction to obtain accurate velocities, however the angle correction vector may be subjective, thus also prone to operator errors. Thus, this method has high variability, limited accuracy, makes geometric assumptions, and is not operator friendly. Furthermore, total flow estimated using this method is not a true three dimensional (3D) measurement.

To overcome the above limitations, a 3D ultrasound method for measuring volume blood flow has been developed as described in U.S. Pat. Nos. 6,535,835, 6,780,155, and O. D. Kripfgans, J. M. Rubin, A. L. Hall, M. B. Gordon, and J. B. Fowlkes, "Measurement of Volumetric Flow," J Ultrasound Med 2006; 25:1305-1311, which are incorporated herein by reference for any purpose. The method performs a surface integration of velocity vectors from the Doppler data based on Gauss' theorem. It may be implemented by defining a surface called a Gaussian surface that is locally perpendicular to the ultrasound beam (also referred to as a C-plane or Z-surface). In each of the Gaussian surfaces (Z-surfaces or C-planes) an integral of the product of velocity and surface area provide a total flow through the Gaussian surface. The calculation of this method must be limited to a blood vessel of interest. In addition, limited resolution of the ultrasound voxels produces partial volume effects at the boundary of the blood vessel. These are corrected for by using a Doppler power based weighting. While Doppler data is available from all spatial locations in the 3D volume, potentially only a single cross-section is enough to estimate the total volumetric flow. Multiple Z-surfaces may be used to improve robustness. The measurements at multiple Z-surfaces may be used to obtain a mean estimate of the volume flow. However, the data from these Z-surfaces could be of variable quality. The variability affects the repeatability of the measurements and usability of the measurements for diagnostic purposes.

SUMMARY

Apparatuses, systems, and methods for providing user feedback on acquisition of ultrasound data are disclosed herein. The ultrasound data may include Doppler data used for calculating volume flow, such as blood flow through one or more blood vessels. The feedback may indicate a quality of the acquisition and/or the reliability of the measurements calculated from the ultrasound data, for example, the volume flow measurements calculated from Doppler data. In some examples, a signal-to-noise ratio (SNR) may be calculated to provide an indication of quality of the acquisition. In some examples, motion of the ultrasound probe and/or subject may be detected to provide an indication of quality. In some examples, Doppler angle, vessel size, and/or vessel depth may be determined to provide an indication of quality. In some examples, variance in velocities in the blood vessels may be determined to provide an indication of quality. In some examples, the SNR and/or other quality factors may be provided to the user. In some examples, one or more of the quality factors may be combined into a quality indicator (e.g., index). In some examples, a qualitative indication of the quality of the acquisition may be provided to the user.

In accordance with at least one example disclosed herein, an ultrasound imaging system may be configured to provide feedback on a quality of volume flow measurements, and the system may include a user interface, a non-transitory computer readable medium encoded with instructions and configured to store power Doppler data for a plurality of Z-surfaces of a volume including a region of interest (ROI), and at least one processor in communication with the non-transitory computer readable medium configured to execute the instructions, wherein when executed, the instructions cause at least one processor to generate a histogram for individual ones of the plurality of Z-surfaces based, at least in part, on the power Doppler data, wherein the histogram has a first curve based on the power Doppler data from within the ROI and a second curve based on the power Doppler data from outside the ROI, calculate a signal-to-noise ratio (SNR) in the logarithmic domain by subtracting a peak of the second curve from a peak of the first curve for at least one of the plurality of Z-surfaces, and generate a quality factor based, at least in part, on the SNR, generate display data for a quality indicator based, at least in part, on the quality factor, wherein the quality indicator is indicative of the quality of the volume flow measurements, wherein the user interface is configured to display the quality indicator to a user based on the display data.

In accordance with at least one example disclosed herein, a method for providing feedback on a quality of volume flow measurements may include generating a histogram from power Doppler data for individual ones of a plurality of Z-surfaces in a volume of a subject, wherein the histogram has a first curve based on the power Doppler data from within a region of interest (ROI) and a second curve based on the power Doppler data from outside the ROI, calculating a signal-to-noise ratio (SNR) by subtracting a peak the second curve from a peak of the first curve for at least one of the plurality of Z-surfaces, and generating a quality factor based, at least in part, on the SNR, generating display data for a quality indicator based, at least in part, on the quality factor, wherein the quality indicator is indicative of the quality of the volume flow measurements, and displaying the quality indicator to a user based on the display data.

DESCRIPTION

Figure 1:
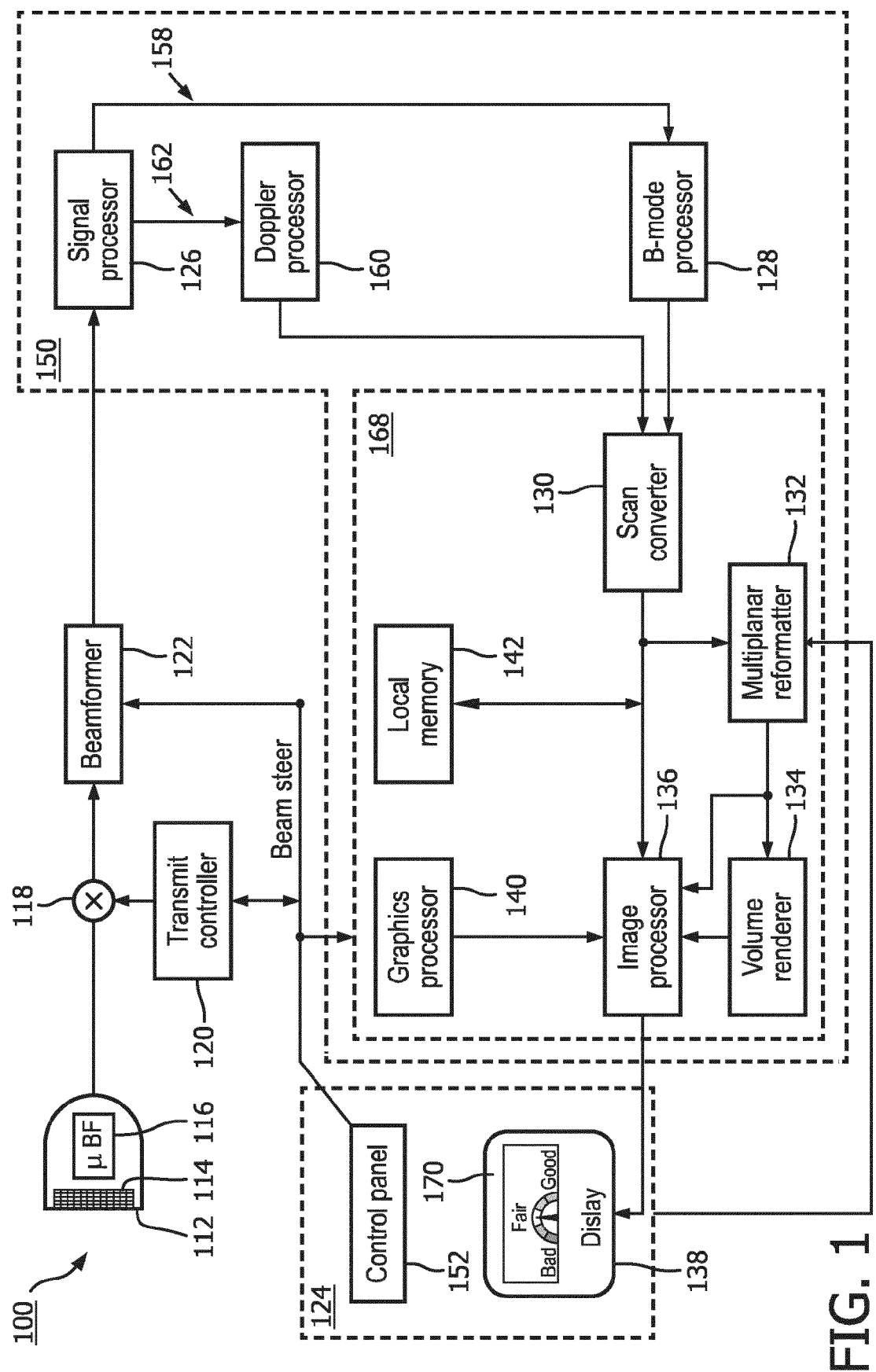
FIG. 1 is a block diagram of an ultrasound imaging system arranged in accordance with principles of the present disclosure.

The following description of certain exemplary examples is merely exemplary in nature and is in no way intended to limit the invention or its applications or uses. In the following detailed description of examples of the present apparatuses, systems and methods, reference is made to the accompanying drawings which form a part hereof, and in which are shown by way of illustration specific examples in which the described apparatuses, systems and methods may be practiced. These examples are described in sufficient detail to enable those skilled in the art to practice the presently disclosed apparatuses, systems and methods, and it is to be understood that other examples may be utilized and that structural and logical changes may be made without departing from the spirit and scope of the present disclosure. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Blood volume flow quantification features currently on commercial ultrasound imaging systems are based on two dimensional (2D) pulsed wave Doppler (e.g., spectral Doppler) measurements. As described in the Background, techniques for 3D volume flow measurements have been developed and will likely be implemented on commercial ultrasound imaging systems in the future. The techniques for 3D volume flow measurements have the potential for quick, accurate, and reliable quantification of volume flow. However, the volume flow quantification results are dependent on the quality of the acquisition of the ultrasound data (e.g., Doppler data). There are multiple factors that may affect the quality of the acquisitions such as motion, attenuation, Doppler angle, vessel size, vessel depth, and/or improper imaging settings (e.g., focus, gain, pulse repetition frequency).

Because 3D volume flow is a new measurement not yet widely available, users do not have experience acquiring data for generating volume flow measurements nor an understanding of how to achieve quality (e.g., accurate/reliable, repeatable) results. While users may be familiar with assessing the quality of the spectral trace in 2D Doppler, there is no such equivalence for 3D volume flow. Currently, there is a lack of a feedback mechanism that users can understand that provides information regarding the quality of the acquisition (e.g., the Doppler data to generate the volume flow measurements). This lack of feedback may lead to poor reliability and/or repeatability of volume flow measurements (e.g., poor quality of the volume flow measurements). Such poor measurements may lead to failed exams. Therefore, a meaningful and easy-to-understand feedback mechanism for data acquisition may be desirable.

The present disclosure is directed to apparatuses, systems, and methods for providing feedback to a user including an indication of a quality of an acquisition of data. For example, the quality of Doppler data acquired by the user with an ultrasound probe. The indication of quality (e.g., quality indicator) may be based on one or more quality factors. Quality factors may include, but are not limited to, SNR, size of blood vessel, location (e.g., depth) of blood vessel, motion of the probe and/or subject, variance in velocity values, and/or Doppler angle. Examples for calculation of these quality factors and generating one or more quality indicators are described in more detail herein. In some examples, feedback may be provided to the user to provide suggestions for improving the quality of the acquisition. For example, if motion is detected, the feedback may alert the user to hold the ultrasound probe steady or advise the subject to remain still. In another example, if a sub-optimal Doppler angle is determined, the feedback may advise the user to adjust an angle of the ultrasound probe. In some applications, the quality of the acquisition may be an indication of the accuracy, reliability, and/or repeatability of measurements generated from the acquired data. For example, measurements may include volume flow measurements generated from the acquired Doppler data. The feedback may encourage users to reacquire data during an exam if the original data acquisition was poor, which may lead to more accurate and/or repeatable measurements. In some applications, the feedback may help users improve their data acquisition techniques, which may reduce the need to reacquire data.

FIG. 1 shows a block diagram of an ultrasound imaging system 100 constructed in accordance with the principles of the present disclosure. An ultrasound imaging system 100 according to the present disclosure may include a transducer array 114, which may be included in an ultrasound probe 112, for example an external probe or an internal probe. The transducer array 114 is configured to transmit ultrasound signals (e.g., beams, waves) and receive echoes (e.g., received ultrasound signals) responsive to the transmitted ultrasound signals. A variety of transducer arrays may be used, e.g., linear arrays, curved arrays, or phased arrays. The transducer array 114, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some examples, the transducer array 114 may be coupled to a microbeamformer 116, which may be located in the ultrasound probe 112, and which may control the transmission and reception of signals by the transducer elements in the array 114. In some examples, the microbeamformer 116 may control the transmission and reception of signals by active elements in the array 114 (e.g., an active subset of elements of the array that define the active aperture at any given time).

In some examples, the microbeamformer 116 may be coupled, e.g., by a probe cable or wirelessly, to a transmit/receive (T/R) switch 118, which switches between transmission and reception and protects the main beamformer 122 from high energy transmit signals. In some examples, for example in portable ultrasound systems, the T/R switch 118 and other elements in the system can be included in the ultrasound probe 112 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 114 under control of the microbeamformer 116 is directed by the transmit controller 120, which may be coupled to the T/R switch 118 and a main beamformer 122. The transmit controller 120 may control the direction in which beams are steered. Beams may be steered straight ahead from (orthogonal to) the transducer array 114, or at different angles for a wider field of view. The transmit controller 120 may also be coupled to a user interface 124 and receive input from the user's operation of a user control. The user interface 124 may include one or more input devices such as a control panel 152, which may include one or more mechanical controls (e.g., buttons, encoders, etc.), touch sensitive controls (e.g., a trackpad, a touchscreen, or the like), and/or other known input devices.

In some examples, the partially beamformed signals produced by the microbeamformer 116 may be coupled to a main beamformer 122 where partially beamformed signals from individual patches of transducer elements may be combined into a fully beamformed signal. In some examples, microbeamformer 116 is omitted, and the transducer array 114 is under the control of the beamformer 122 and beamformer 122 performs all beamforming of signals. In examples with and without the microbeamformer 116, the beamformed signals of beamformer 122 are coupled to processing circuitry 150, which may include one or more processors (e.g., a signal processor 126, a B-mode processor 128, a Doppler processor 160, and one or more image generation and processing components 168) configured to produce an ultrasound image from the beamformed signals (i.e., beamformed RF data).

The signal processor 126 may be configured to process the received beamformed RF data in various ways, such as bandpass filtering, decimation, I and Q component separation, and harmonic signal separation. The signal processor 126 may also perform additional signal enhancement such as speckle reduction, signal compounding, and electronic noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, contrast image data, Doppler image data). For example, the system 100 may include a B-mode signal path 158 which couples the signals from the signal processor 126 to a B-mode processor 128 for producing B-mode image data. The B-mode processor 128 can employ amplitude detection for the imaging of organ structures the body.

In some examples, the system may include a Doppler signal path 162 which couples the output from the signal processor 126 to a Doppler processor 160. The Doppler processor 160 may be configured to estimate the Doppler shift and generate Doppler image data. The Doppler image data may include color data which is then overlaid with B-mode (e.g., grayscale) image data for display. The Doppler processor 160 may be configured to filter out unwanted signals (e.g., noise or clutter associated with non-moving tissue), for example using a wall filter. The Doppler processor 160 may be further configured to estimate velocity and power in accordance with known techniques. For example, the Doppler processor may include a Doppler estimator such as an auto-correlator, in which velocity (Doppler frequency, spectral Doppler, color Doppler) estimation is based on the argument of the lag-one (R1) autocorrelation function and Doppler power estimation is based on the magnitude of the lag-zero (R0) autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo further threshold detection to further reduce noise, as well as segmentation and post-processing such as filling and smoothing. The velocity and power estimates may then be mapped to a desired range of display colors in accordance with a color map. The color data, also referred to as Doppler image data, may then be coupled to the scan converter 130, where the Doppler image data may be converted to the desired image format and overlaid on the B-mode image of the tissue structure to form a color Doppler or a power Doppler image. For example, Doppler image data may be overlaid on a B-mode image of the tissue structure.

The signals produced by the B-mode processor 128 and/or Doppler processor 160 may be coupled to a scan converter 130 and/or a multiplanar reformatter 132. The scan converter 130 may be configured to arrange the echo signals from the spatial relationship in which they were received to a desired image format. For instance, the scan converter 130 may arrange the echo signal into a two dimensional (2D) sector-shaped format, or a pyramidal or otherwise shaped three dimensional (3D) format. The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). The scan converter 130 and multiplanar reformatter 132 may be implemented as one or more processors in some examples.

A volume renderer 134 may generate an image (also referred to as a projection, render, or rendering) of the 3D dataset as viewed from a given reference point, e.g., as described in U.S. Pat. No. 6,530,885 (Entrekin et al.). The volume renderer 134 may be implemented as one or more processors in some examples. The volume renderer 134 may generate a render, such as a positive render or a negative render, by any known or future known technique such as surface rendering and maximum intensity rendering. Although shown in FIG. 1 as receiving data from the multiplanar reformatter 132, in some examples, the volume renderer 134 may receive data from the scan converter 130.

Output (e.g., B-mode images, Doppler images) from the scan converter 130, the multiplanar reformatter 132, and/or the volume renderer 134 may be coupled to an image processor 136 for further enhancement, buffering and temporary storage before being displayed on an image display 138. A graphics processor 140 may generate graphic overlays for display with images, such as the accumulation image generated by the image processor 136. These graphic overlays can contain, e.g., standard identifying information such as patient name, date and time of the image, imaging parameters, and the like. For these purposes the graphics processor may be configured to receive input from the user interface 124, such as a typed patient name or other annotations. The user interface 124 can also be coupled to the multiplanar reformatter 132 for selection and control of a display of multiple multiplanar reformatted (MPR) images.

The system 100 may include local memory 142. Local memory 142 may be implemented as any suitable non-transitory computer readable medium or media (e.g., flash drive, disk drive, dynamic random access memory). Local memory 142 may store data generated by the system 100 including B-mode images, Doppler images, instructions capable of being executed by one or more of the processors included in the system 100 (e.g., Doppler processor 160, image processor 136), inputs provided by a user via the user interface 124, or any other information necessary for the operation of the system 100.

As mentioned previously, system 100 includes user interface 124. User interface 124 may include display 138 and control panel 152. The display 138 may include a display device implemented using a variety of known display technologies, such as LCD, LED, OLED, or plasma display technology. In some examples, display 138 may comprise multiple displays. The control panel 152 may be configured to receive user inputs (e.g., exam type, selection of ROI in image). The control panel 152 may include one or more hard controls (e.g., buttons, knobs, dials, encoders, mouse, trackball or others). In some examples, the control panel 152 may additionally or alternatively include soft controls (e.g., GUI control elements or simply, GUI controls) provided on a touch sensitive display. In some examples, display 138 may be a touch sensitive display that includes one or more soft controls of the control panel 152.

In some examples, various components shown in FIG. 1 may be combined. For instance, image processor 136 and graphics processor 140 may be implemented as a single processor. In another example, the scan converter 130 and multiplanar reformatter 132 may be implemented as a single processor. In some examples, various components shown in FIG. 1 may be implemented as separate components. For example, image processor 136 may be implemented as multiple processors. In some examples, the multiple image processors may perform different tasks (e.g., image segmentation, SNR calculation, motion detection, etc.). In another example, local memory 142 may include multiple memories which may be the same or different memory types (e.g., flash, DRAM).

In some examples, one or more of the various processors shown in FIG. 1 may be implemented by general purpose processors and/or microprocessors configured to perform the specified tasks. For example, the processors may be configured by instructions stored in a non-transitory computer readable memory (e.g., local memory 142) which are executed by the processors to perform the specified tasks. In some examples, one or more of the various processors may be implemented as application specific circuits (ASICs). In some examples, one or more of the various processors (e.g., image processor 136) may be implemented with one or more graphical processing units (GPU).

For acquiring volume flow measurements, the probe 112 may acquire volume (e.g., 3D) ultrasound data (e.g., B-mode data, Doppler data) with one or more blood vessels in a field of view. The volume ultrasound data may be acquired continuously such that there is sufficient spatial and temporal coverage of a region of interest (ROI) including one or more vessels. In some applications, the ROI may be sampled at a sufficient temporal rate to cover a cardiac cycle (e.g., heart beat). In some examples, the ROI may be selected by a user via the user interface 124. In some examples, the user may select the ROI prior to collection of volume Doppler data. For example, a 2D or 3D ultrasound image may be acquired, and the user may select an ROI from the 2D or 3D ultrasound image. In other examples, the entire field of view may be sampled sufficiently temporally and spatially, and a user may select an ROI after the volume ultrasound data has been acquired.

In some examples, the field of view and/or ROI may be divided into sub-volumes. In some applications, acquiring volume ultrasound data from the sub-volumes may require less time than a complete volume. The volume ultrasound data from the sub-volumes may be acquired continuously over multiple cardiac cycles in some examples. The acquired volume ultrasound data from the sub-volumes may be retrospectively stitched together in order to generate a full volume with adequate temporal sampling. The acquisition may capture both constant and pulsatile flow profiles in some examples. The dividing and stitching may be performed by the signal processor 126, Doppler processor 160, B-mode processor 128, scan converter 130, and/or image processor 136 in some examples.

At least some of the ultrasound beams transmitted by the probe 112 may intersect a blood vessel in the ROI such that a Z-surface (e.g., Gaussian plane) can be defined including the entire cross-section of the vessel that has points equidistant to the probe 112 surface. The Z-surface may have a certain depth. In a volumetric acquisition, there may be multiple such Z-surfaces that include complete cross-sections of the blood vessel. Some or all of the Z-surfaces may be utilized for the volume flow measurement computations.

In each of those Z-surfaces, the blood vessel of interest may be either manually or automatically segmented. Manual segmentation may involve a user, via the user interface 124, placing an ROI around the vessel boundary that encompasses the blood vessel as seen by the user in Doppler velocity (e.g., spectral) and/or Doppler power images provided on display 138. Automatic segmentation may involve a combination of threshold and other morphological image processing operations on the individual power, velocity or B-Mode images or a combination of the above to set the ROI to the vessel boundary in the volume ultrasound data. Segmentation could also or alternatively involve artificial intelligence algorithms that identifies the vessel across multiple Z-surfaces in the volume ultrasound data. The segmenting may be performed by the image processor 136 in some examples.

Once the vessel boundary is segmented, power Doppler values in the pixels inside and outside the vessel may be utilized to compute a histogram in some examples. For example, the histogram may include one curve (e.g., profile) of power Doppler values located within the ROI (e.g., within the blood vessel) in a Z-surface and another curve of power Doppler values located outside the ROI in the Z-surface. The power Doppler histogram method may be utilized to derive fractional weights that determines regions of voxels inside and outside the vessel as well as partial volume voxels on the boundary with fractional weights. That is, some voxels on the border of the vessel may include data from both inside the vessel and tissue outside the vessel. Once the partial volume weights are determined from the power Doppler histogram, the velocity from the spectral Doppler data and surface area of the voxels may be multiplied to obtain volumetric flow in the individual voxels. An integral of the flow values in the voxels inside the vessel gives the volumetric flow in that Z-surface. These volume flow values may be stored, for example, in local memory 142, and/or provided to the user on display 138.

According to principles of the present disclosure, in addition to providing the volume flow measurements, the system 100 may provide an indication of quality of the volume flow measurements with a quality indicator 170 to the user, for example, as text or a graphic on display 138. The quality indicator 170 may indicate a level of reliability/accuracy and/or repeatability of the volume flow measurements. In some examples, the quality indicator 170 may provide a qualitative indication of quality of the acquisition. For example, the quality indicator 170 may provide different colors, shapes, or descriptors/adjectives (e.g., good, fair, bad) to indicate the quality of the acquisition. In some examples, the quality indicator 170 may provide a quantitative value indicating the quality of the acquisition. The indication of quality may be based, at least in part, on one or more quality factors. Quality factors may include, but are not limited to, SNR, presence of motion (e.g., detection of motion), Doppler angle, vessel size, vessel depth, and/or variance of flow velocity inside the vessel.

In some examples, multiple quality factors may be combined to generate the indication of quality provided by the quality indicator 170. In some examples, only one of the quality factors may be used to generate the indication of quality. In some examples, one or more quality factors may be used to generate the indication of quality while the same or different quality factors may be used to provide guidance to a user for improving the acquisition. For example, the SNR may be used to determine the indication of quality provided by the quality indicator 170 while Doppler angle may be used to provide guidance to the user to adjust the orientation of the probe 112. In some examples, the quality indicator 170 may also provide the guidance.

Figure 2:
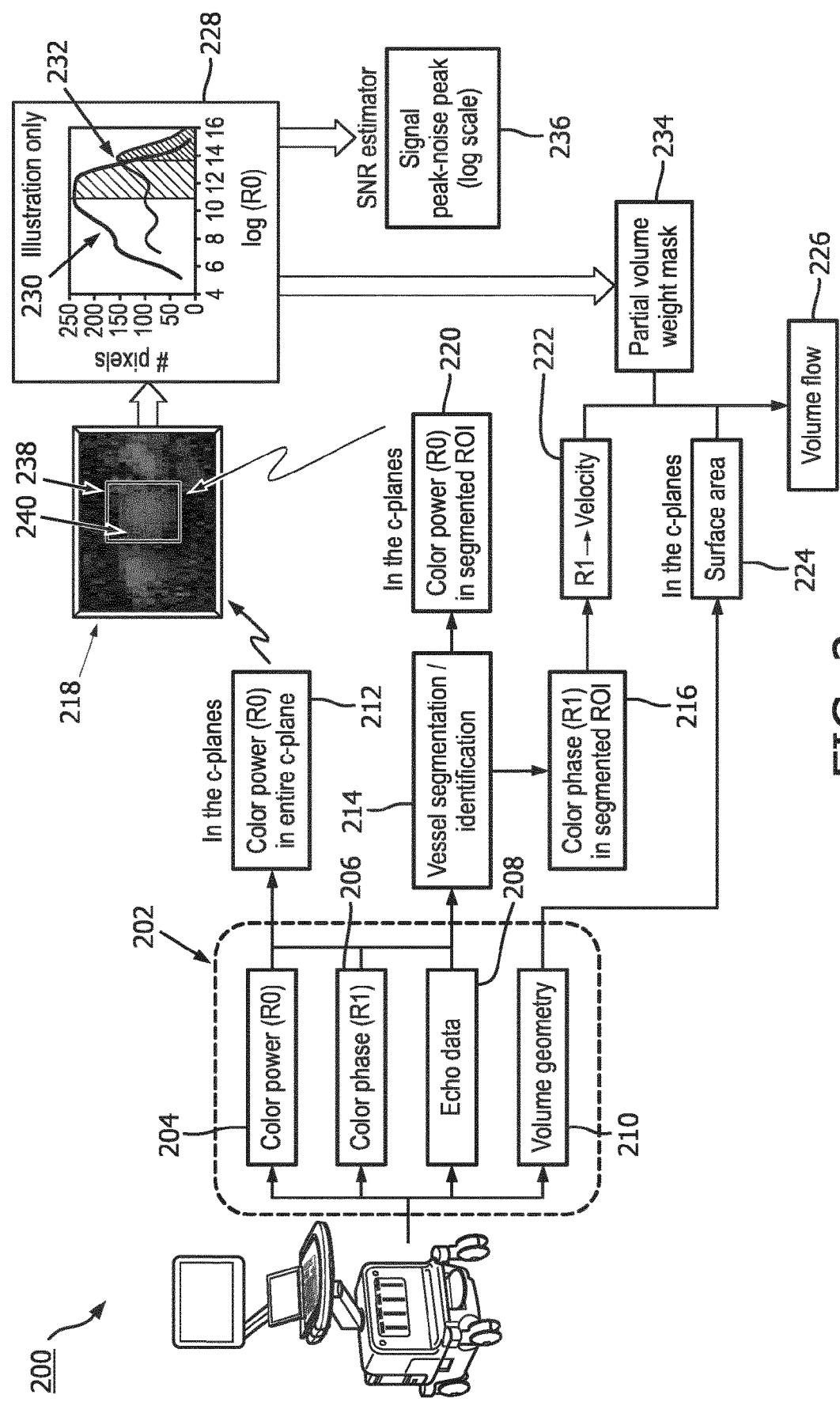
FIG. 2 is a block diagram illustrating a method to calculate the signal-to-noise ratio from Doppler data acquired for three dimensional volume flow quantification according to principles of the present disclosure.

In some examples, SNR may be the main quality factor used to determine the quality of the acquisition. FIG. 2 is a block diagram illustrating a method to calculate the signal-to-noise ratio from Doppler data acquired for three dimensional volume flow quantification according to principles of the present disclosure. An ultrasound imaging system 200, may acquire image data 202 from a volume within a subject. The ultrasound imaging system 200 may be included in or used to implement system 100 in some examples. The image data 202 may include power Doppler data 204, which may be color power Doppler data in some examples, such as the one shown in FIG. 2. The image data 202 may include color spectral Doppler data 206 (e.g., color phase), echo data 208 (e.g., B-mode data), and/or volume geometry 210. In some examples, the image data 202 may have been acquired by a transducer array of a probe, such as transducer array 114 of probe 112. In some examples, the power Doppler data 204 and/or spectral Doppler data 206 may be extracted from the image data 202 by a Doppler processor, such as Doppler processor 160. In some examples, the echo data 208 may be extracted from the image data (e.g., acquisition data) 202 by a B-mode processor such as B-mode processor 128. In some examples, the volume geometry 210 may be provided by a scan converter, multiplanar reformatter, and/or volume renderer, such as scan converter 130, multiplanar reformatter 132, and/or volume renderer 134. In some examples, the computations on the image data 202 may be performed by one or more processors, for example, image processor 136, Doppler processor 160, B-mode processor 128, scan converter 130, multiplanar reformatter 132, and/or volume renderer 134.

As shown in FIG. 2, in some examples, the power Doppler data 204 may be used to provide the power Doppler data in individual Z-surfaces 212 in the volume and/or in a ROI within the volume. In some examples, the power Doppler data 204, color Doppler data 206, and/or echo data 208 may be used to segment and/or identify one or more blood vessels (e.g., vessel segmentation 214) within the volume and/or ROI. In some examples, the segmentation may be performed by an image processor, such as image processor 136. In some examples, the segmentation of a vessel from the volume may be used to set the ROI within the volume. In other examples, a user may define the ROI (e.g., via a user interface, such as user interface 124), and the one or more blood vessels may be segmented from the ROI.

The vessel segmentation may be used to access the color velocities within the one or more vessels. The volume geometry 210 may be used to calculate the surface area 224 of every Z-surface within the volume and/or ROI.

The vessel segmentation 214 may also be used to access the power Doppler data within the vessel ROI 220. Doppler image 218 is an image of a Z-surface with an ROI 238 including a blood vessel 240. The power Doppler data in the entire Z-surface 212 and the power Doppler within the ROI 220 may be used to generate a power Doppler histogram 228. The histogram peak 230 of power Doppler data outside the ROI 238 represents the noise and the histogram peak 232 of power Doppler data within the ROI 220 represents the signal of interest.

The data from the histogram 228 may be used to generate a partial volume weight mask 234. The partial volume weight mask 234 may be combined with the velocity 222 and surface area 224 data to provide volume flow measurements 226. The data from the power Doppler histogram 228 may be used to calculate the SNR 236 in some examples. As noted, the Doppler histogram 228 may have a curve based on the power Doppler data from within the ROI (signal) and a curve based on the power Doppler data from outside the ROI (noise). In some examples, in a logarithmic scale (e.g., decibels dB), the difference between the signal and the noise peaks represent the SNR of the Z-surface (e.g., $SNR=Signal_{peak}-Noise_{peak}$). Thus, an SNR for each Z-surface may be computed and stored. For example, data may be stored in a local memory, such as local memory 142.

The SNR values in multiple Z-surfaces along the depth may present some variation on account of non-uniformity in the ultrasound beam intensities, structures in the field of view causing reflections and reverberations, attenuation, and other factors that affect the quality of the Z-surfaces. For example, at certain depths there may be reflections leading to higher noise in the regions outside the vessel. Similarly, the beam angle and/or the attenuation may cause a diminished value of the signal inside the vessel. To determine the quality of the acquisition based on these multiple and variable SNR values, one or techniques may be used to identify a set of Z-surfaces whose SNR values are used to determine the quality factor for the acquisition. In some examples, the Z-surfaces may be sorted based on the SNR values. In some examples, the mean and/or median SNR for all the Z-surfaces of the vessel within the ROI may be provided as the quality factor (e.g., dB).

In some examples, interquartile range median (IQR/Median) may be used to determine what range of data Z-surfaces are used in combination with the mean or median to determine the SNR. The interquartile range (IQR) is a measure of variability, based on dividing a data set into quartiles (e.g., the SNRs for the Z-surfaces). The top and bottom quartiles are removed from the data set, thus leaving the "middle fifty" around the median of the data set. The interquartile range divided by the median value provides a quality factor. For example, among the SNR sorted Z-surfaces, using Z-surface groups of greater than five such as 1-5, 1-6, 1-7, etc., IQR/Med of the SNR are computed: $IQR_{1-5}$, $IQR_{1-6}$, $IQR_{1-7}$, and so on. The mean or median SNR of the group that has the minimum IQR/Med is selected as the one to provide as the quality factor based on SNR.

In some examples, coefficient of variation (COV) or relative standard deviation (e.g., the standard deviation divided by the mean) may be used to determine the range of data (e.g., which SNR values of the Z-surfaces) to be used in combination with the mean or median. For example, among the SNR sorted Z-surfaces, using Z-surface groups of greater than three such as 1-3, 1-4, 1-5, etc., the COV of the SNR values are computed: $COV_{1-3}$, $COV_{1-4}$, $COV_{1-5}$, etc. The mean or median of the group of Z-surfaces that represents the minimum COV may be selected as the one used to generate the quality factor based on SNR.

In another example, the mean SNR of a few Z-surfaces (e.g., 3, 5, 10) closest to and/or proximate the focus of the ultrasound beam provided by the ultrasound probe 112 may be used.

In some examples, multiple ones of the techniques for determining the SNR and/or which SNR values to use may be combined to generate the quality factor. For example, an average SNR calculated from the various techniques may be used for the quality factor. In some examples, the different SNR values determined by the different techniques may be weighted differently when computing the average. In some examples, SNR values calculated by different techniques may be provided as separate quality factors used to determine an indication of quality provided by a quality indicator, such as quality indicator 170. In some examples, SNR may be the only quality factor used to generate the indication of quality.

Figure 3A:
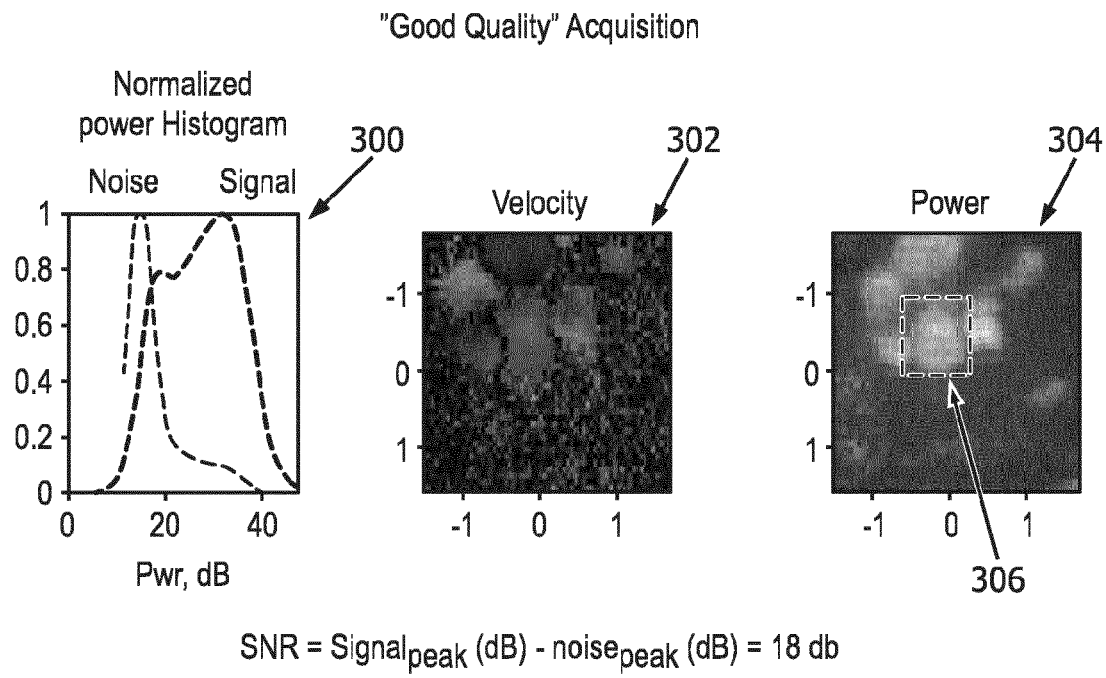
FIGS. 3A-3B illustrates examples images of color and power Doppler data acquisitions and corresponding power histograms for calculating the signal-to-noise ratio according to principles of the present disclosure.
Figure 3B:
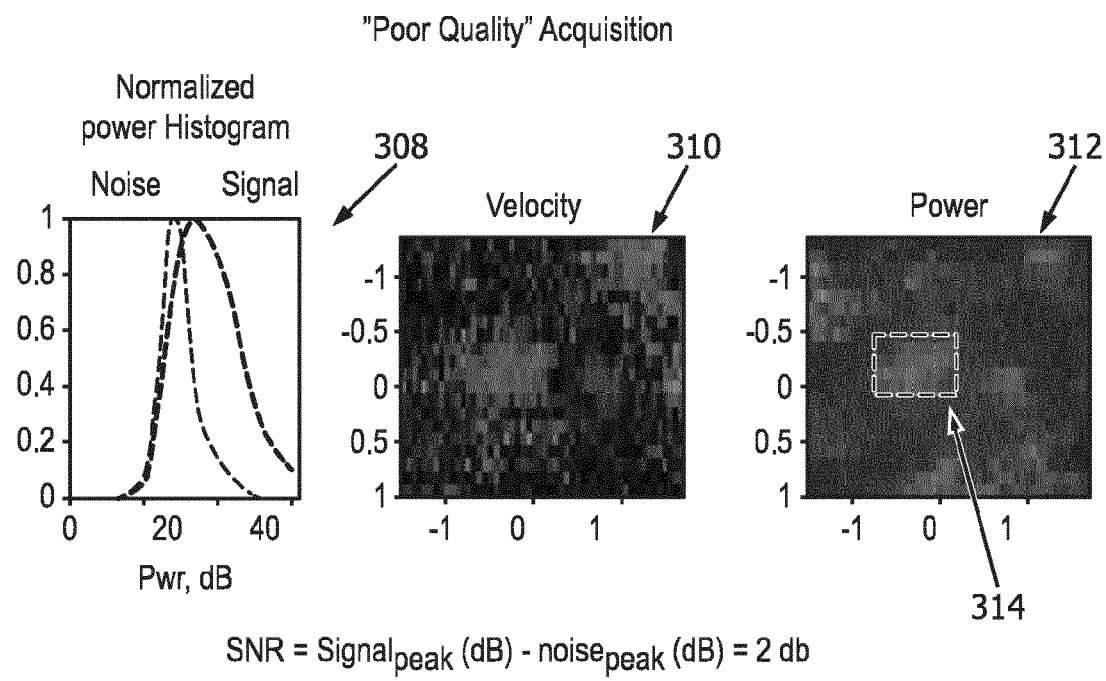

FIGS. 3A-3B illustrates examples images of spectral and power Doppler data acquisitions and corresponding power histograms for calculating the signal-to-noise ratio according to principles of the present disclosure. The images and histograms may have been generated by an ultrasound imaging system, such as ultrasound imaging system 100 and/or ultrasound imaging system 200.

In FIG. 3A, a velocity map generated from color Doppler velocity data for a Z-surface is shown in image 302, and a power Doppler map for the same Z-surface is shown in image 304 for a same acquisition. A vessel is shown within a ROI 302 in image 304. Histogram 300 is a plot of power Doppler data showing curves for the noise (e.g., power Doppler data outside the ROI 306) and the signal (e.g., power Doppler data inside the ROI 306). Below the images the difference in power (dB) between the signal and noise peaks, the SNR, which is 18 dB.

In FIG. 3B, a velocity map generated from color Doppler velocity data for a Z-surface is shown in image 310, and a power Doppler map for the same Z-surface is shown in image 312 for another acquisition. A vessel is shown within a ROI 314 in image 312. Histogram 308 is a plot of power Doppler data showing curves for the noise (e.g., power Doppler data outside the ROI 314) and the signal (e.g., power Doppler data inside the ROI 314). The velocity map 310 has less well-defined vessels compared to the velocity map 302. Furthermore, the power Doppler map 312 has less contrast than the power Doppler map 304. Below the images the difference in power (dB) between the signal and noise peaks, the SNR, which is 2 dB, much lower than the SNR for FIG. 3A.

The data shown in FIGS. 3A and 3B were from umbilical cord images. In this application, good quality acquisitions were associated with SNR of 12 dB and higher. However, different ranges of SNR may be used to classify the quality of the acquisition (e.g., 0-5 dB bad, 6-14 dB fair, 15-20 dB good, 20-24 dB better, 25+dB great). The SNR may be used to generate a quantitative quality indicator. For example, the numerical value (e.g., in dB) may be provided on a quality indicator (e.g., quality indicator 170). In some examples, the SNR may be used to generate a qualitative quality indicator, for example, different colors and/or other descriptors may be associated with different ranges of SNR values.

Other quality factors in addition to the SNR may also be determined in other examples to compute the indication of quality and/or provide advice to a user to improve quality of the acquisition.

In some examples, the size and/or depth of the blood vessel may be determined from the segmented data. Vessels with smaller diameters imaged with a broad Doppler ultrasound beam may be resolution limited. That is, there may not be enough ultrasound beams inside the blood vessel, which may limit the effectiveness of the partial volume correction algorithms. Similarly, a deeper vessel may be affected by an increased attenuation and/or diminished power inside the vessel. In addition, a deeper vessel interacting with a diverging beam may again be resolution limited. The effect on the partial volumes weights caused by both the size and depth of the vessel may limit the accuracy and may increase the variability in the volume flow measurements. Thus, small and/or deep vessels may provide lower valued quality factors for determining the indication of quality. In some examples, based on the ultrasound beam profile, depth and size of the vessel, a table of weights can be computed and used in the quality factor.

Additionally or alternatively to being used for the indication of quality, the determination may be used to provide suggestions to the user for improving the acquisition. For example, if a vessel diameter and/or beam density within the vessel is below a threshold value, the ultrasound system, such as system 100, may prompt the user to select a different vessel and/or imaging settings (e.g., increase beam density) to acquire flow measurements. Prompting the user may be through text, graphics, audio signals, and/or haptic feedback (e.g., probe vibrations). In another example, if a vessel depth and/or power level within the vessel is below a threshold value, the system may prompt the user to select a different vessel and/or imaging setting (e.g., increase power).

In some examples, the effect of motion on the Doppler data may be taken into account as a quality factor for the indication of quality and/or user suggestions. In the iSTIC acquisition framework, each sub-volume (e.g., elevation planes(s)) may be continuously sampled with high temporal resolution through the cardiac cycle. This may then be repeated for the rest of the sub-volumes. Data affected by motion may have decreased robustness of the segmented boundary of the vessel as visualized on the Z-surfaces through the cardiac cycle. Furthermore, there could be increased flash artifacts on the velocity map and/or an increase in transient reflections affecting the power map. Any method for detecting motion known now or in the future may be used. Greater motion may lead to lower valued quality factors. In some examples, if motion is above a threshold (e.g., velocity and/or magnitude of displacement), the ultrasound system may prompt the user to hold the probe still and/or ask the subject to remain still.

In some applications, the Doppler angle may also be an important parameter that has potential implications on the partial volume correction at the boundaries of the vessel, and thus may be an important quality factor. As the angle between the ultrasound beam and the flow axis increases, the number of beams completely inside the vessel decreases. This increases the partial volume beams interacting with the boundary of the vessel. Consequently, similar to effects in small vessels, a resolution limited condition could adversely affect the volume flow measurement accuracy. In some examples, the Doppler angle may be provided as a quality factor. Additionally or alternatively, if the Doppler angle is over a threshold value (e.g., 60 degrees, 65 degrees), the ultrasound system may prompt the user to adjust an angle of the probe to reduce the Doppler angle.

In some applications, an increase in the variance of the velocity values inside the segmented vessel may indicate a poor quality acquisition. The variance of the velocity values may be calculated for each Z-surface in some examples. In some examples, the mean and/or median variance of the Z-surfaces may be provided as the quality factor. In some examples, selection of which Z-surfaces to use to provide the velocity variance factor may be performed using one or more of the techniques described with reference to the SNR.

Figure 4:
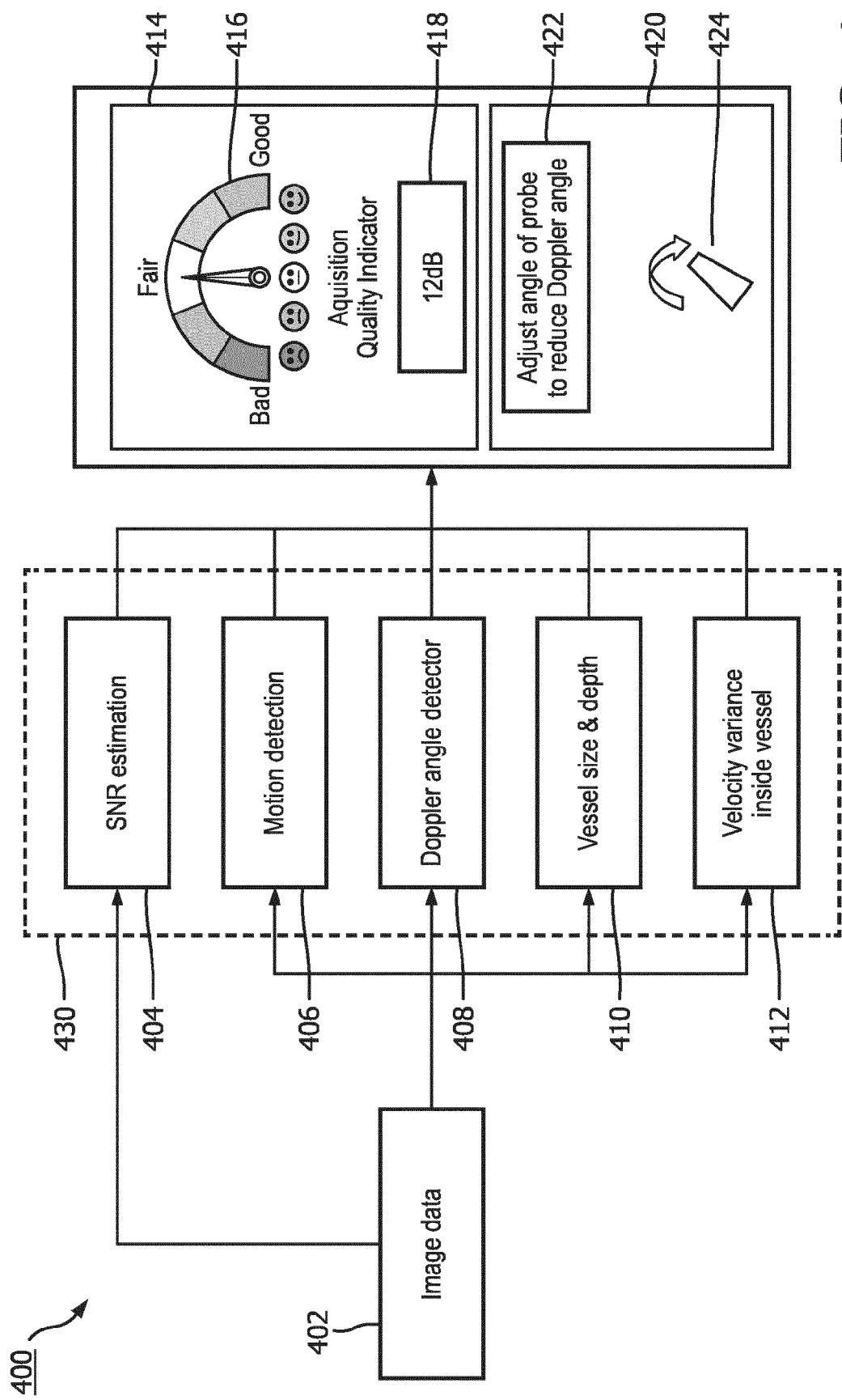
FIG. 4 is a block diagram illustrating an overview of providing an indication of quality of an acquisition according to principles of the present disclosure.

FIG. 4 is a block diagram illustrating an overview of providing an indication of quality of an acquisition according to principles of the present disclosure. The overview 400 may be implemented on an ultrasound imaging system, such as ultrasound imaging system 100 and/or 200.

Image data 402 may have been acquired by a transducer array, such as transducer array 114. In some examples image data 402 may include image data 202. Image data 402 may be used to generate a variety of quality factors 430 such as SNR 404, motion detection 406, Doppler angle 408, vessel size and/or depth 410, and/or velocity variance inside the vessel 412. The quality factors 430 may be used to generate a quality indicator 414 and/or user suggestions 420, which may be provided to a user via a user interface, such as user interface 124.

In some examples, the quality indicator 414 may include text, graphics, sounds, animations, and/or lights (e.g., light emitting diodes). In some examples, the quality indicator 414 may be provided on a display, such as display 138. In some examples, quality indicator 414 may be used to implement quality indicator 170.

In some examples, the quality indicator 414 may include a qualitative and/or semi-qualitative indication of quality of the acquisition of the image data 402. For example, qualitative descriptors (e.g., bad, fair, good), colors (e.g., red, yellow, green), and/or emojis associated with different levels of quality may be used to indicate the quality of the acquisition. An example graphic 416 shows text, shades, a dial, and emojis. However, the graphic 416 is presented merely as an example, and qualitative indicators according to the present disclosure is not limited to the example shown. The qualitative indication may be based on one or more of the quality factors 430.

In some examples, in addition to or instead of a qualitative indication, the quality indicator 414 may provide a quantitative value 418 of quality of the acquisition. In the example shown, the quantitative value 418 is a value of SNR 404 with units in decibels. However, in other examples, the quantitative value 418 may be generated by one or more quality factors 430, which may or may not include the SNR 404.

In some examples, user suggestions 420 may include text, graphics, sounds, animations, and/or lights (e.g., light emitting diodes). In some examples, the user suggestions 420 may be provided on a display, such as display 138. For example, text 422 may provide a suggestion to the user to improve data acquisition. In the example shown in FIG. 4, the text 422 suggests adjusting an angle of the ultrasound probe to improve the Doppler angle (e.g., if the Doppler angle 408 is found to be above a threshold value). As another example, a graphic 424 indicates how the user should move and/or position the ultrasound probe to improve the Doppler angle. Text 422 and graphic 424 are provided merely as examples, and the user suggestions 420 are not limited to the examples shown.

Figure 5:
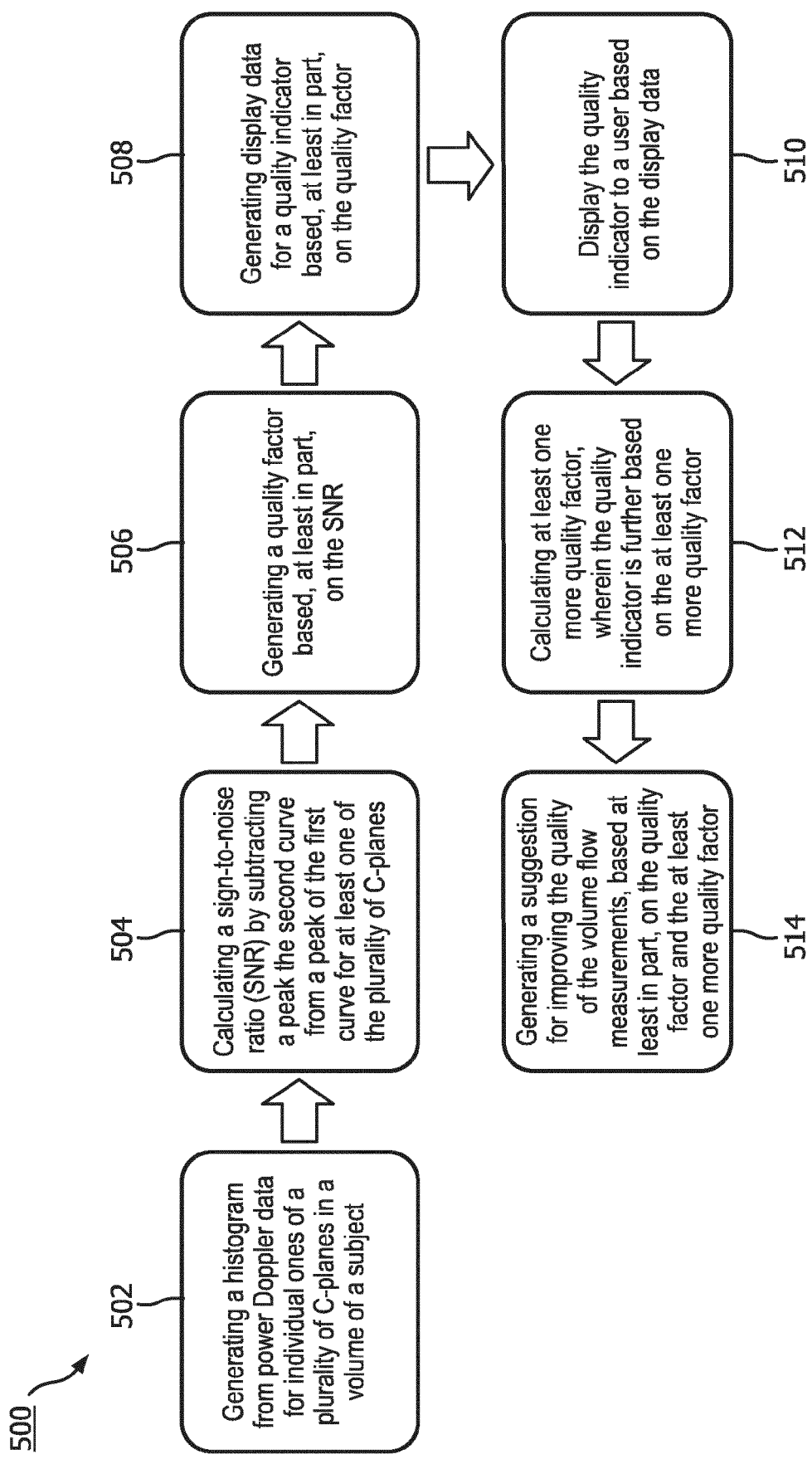
FIG. 5 is a flow chart of a method for providing feedback on a quality of volume flow measurements according to principles of the present disclosure.

FIG. 5 is a flow chart of a method for providing feedback on a quality of volume flow measurements according to principles of the present disclosure. In some examples, the method 500 may be performed, all or in part, by an ultrasound imaging system, such as imaging system 100 and/or imaging system 200. In some examples, the method 500 may be performed by one or more processors executing computer-readable instructions, for example, image processor 136, Doppler processor 160, B-mode processor 128, and/or other processors shown in FIG. 1. In some examples, the computer-readable instructions may be stored in a non-transitory computer-readable medium accessible to the at least one processor, such as local memory 142.

As indicated at block 502, at least one processor, such as image processor 136 may generate a histogram from power Doppler data for individual ones of a plurality of Z-surfaces in a volume of a subject. The power Doppler data may have been acquired by the ultrasound imaging system, for example, by a probe of the ultrasound imaging system. The histogram may have a first curve based on the power Doppler data from within a ROI and a second curve based on the power Doppler data from outside the ROI. The ROI may be based on auto-segmentation of image data from the volume of the subject or based on a user input (e.g., via a user interface, such as user interface 124).

At block 504, the at least one processor may calculate a SNR by subtracting a peak the second curve from a peak of the first curve for at least one of the plurality of Z-surfaces. The at least one processor may then generate a quality factor based, at least in part, on the SNR as indicated by block 506. In some examples, the SNR may be calculated for all Z-surfaces, and an average and/or median SNR may be used to generate the quality factor. In some examples, a subset of the SNR values from the Z-surfaces may be used to generate the quality factor as described with reference to FIGS. 2 and 3.

At block 508, the at least one processor may generate display data for a quality indicator based, at least in part, on the quality factor. The quality indicator may be indicative of the quality of the volume flow measurements. As indicated at block 510, the quality indicator may be displayed to a user based on the display data. For example, the quality indicator may be displayed on display 138. Of course, in other examples, the quality indicator may be an auditory signal provided on a speaker, one or more lights on a control panel of the ultrasound imaging system, and/or haptic feedback provided on the control panel and/or ultrasound probe.

In some examples, the at least one processor may calculate at least one more quality factor, wherein the quality indicator is further based on the at least one more quality factor as shown by block 512. In some examples, as indicated by block 514, the at least one processor may generate a suggestion for improving the quality of the volume flow measurements, based at least in part, on the quality factor and the at least one more quality factor.

Figure 6:
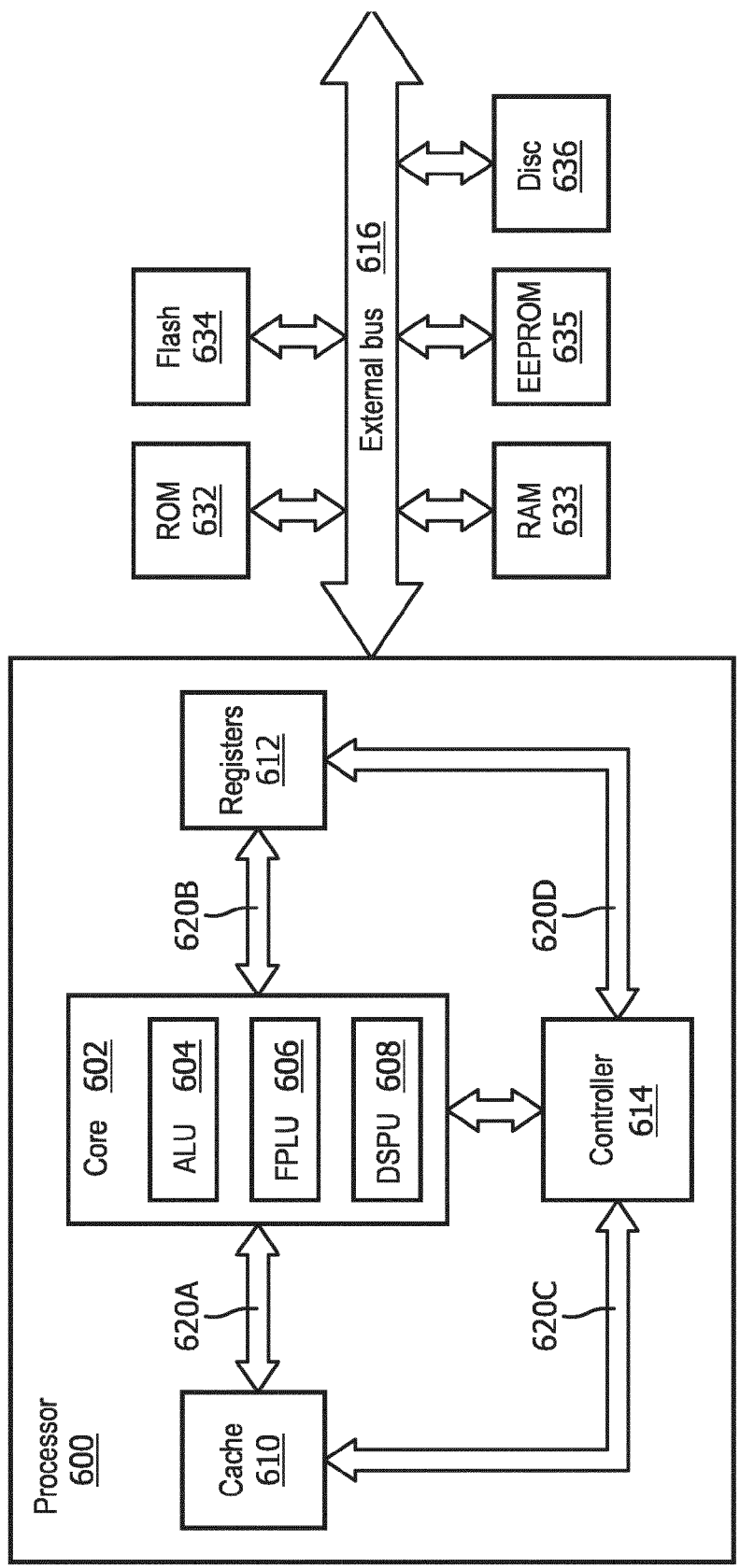
FIG. 6 is a block diagram illustrating an example processor in accordance with principles of the present disclosure.

FIG. 6 is a block diagram illustrating an example processor 600 according to principles of the present disclosure. Processor 600 may be used to implement one or more processors described herein, for example, image processor 136 shown in FIG. 1. Processor 600 may be capable of executing computer-readable instructions stored on a non-transitory computer-readable medium in communication with the processor 600, for example, local memory 142 shown in FIG. 1. Processor 600 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 600 may include one or more cores 602. The core 602 may include one or more arithmetic logic units (ALU) 604. In some examples, the core 602 may include a floating point logic unit (FPLU) 606 and/or a digital signal processing unit (DSPU) 608 in addition to or instead of the ALU 604.

The processor 600 may include one or more registers 612 communicatively coupled to the core 602. The registers 212 may be implemented using dedicated logic gate circuits (e.g., flip-flops) and/or any memory technology. In some examples the registers 612 may be implemented using static memory. The register may provide data, instructions and addresses to the core 602.

In some examples, processor 600 may include one or more levels of cache memory 610 communicatively coupled to the core 602. The cache memory 610 may provide computer-readable instructions to the core 602 for execution. The cache memory 610 may provide data for processing by the core 602. In some examples, the computer-readable instructions may have been provided to the cache memory 610 by a local memory, for example, local memory attached to the external bus 616. The cache memory 610 may be implemented with any suitable cache memory type, for example, metal-oxide semiconductor (MOS) memory such as static random access memory (SRAM), dynamic random access memory (DRAM), and/or any other suitable memory technology.

The processor 600 may include a controller 614, which may control input to the processor 600 from other processors and/or components included in a system (e.g., control panel 152 and scan converter 130 shown in FIG. 1) and/or outputs from the processor 600 to other processors and/or components included in the system (e.g., display 138 and volume renderer 134 shown in FIG. 1). Controller 614 may control the data paths in the ALU 604, FPLU 606 and/or DSPU 608. Controller 614 may be implemented as one or more state machines, data paths and/or dedicated control logic. The gates of controller 614 may be implemented as standalone gates, FPGA, ASIC or any other suitable technology.

The registers 612 and the cache memory 610 may communicate with controller 614 and core 602 via internal connections 620A, 620B, 620C and 620D. Internal connections may implemented as a bus, multiplexor, crossbar switch, and/or any other suitable connection technology.

Inputs and outputs for the processor 600 may be provided via a bus 616, which may include one or more conductive lines. The bus 616 may be communicatively coupled to one or more components of processor 600, for example the controller 614, cache memory 610, and/or register 612. The bus 616 may be coupled to one or more components of the system, such as display 138 and control panel 152 mentioned previously.

The bus 616 may be coupled to one or more external memories. The external memories may include Read Only Memory (ROM) 632. ROM 632 may be a masked ROM, Electronically Programmable Read Only Memory (EPROM) or any other suitable technology. The external memory may include Random Access Memory (RAM) 633. RAM 633 may be a static RAM, battery backed up static RAM, Dynamic RAM (DRAM) or any other suitable technology. The external memory may include Electrically Erasable Programmable Read Only Memory (EEPROM) 635. The external memory may include Flash memory 634. The external memory may include a magnetic storage device such as disc 636. In some examples, the external memories may be included in a system, such as ultrasound imaging system 100 shown in FIG. 1, for example local memory 142.

The apparatuses, systems, and methods disclosed herein may allow for providing feedback to a user including an indication of a quality of an acquisition of data based on one or more quality factors. In some examples, the apparatuses, systems, and methods disclosed herein may allow for providing suggestions for improving the quality of the acquisition to the user. The feedback may encourage users to reacquire data during an exam if the original data acquisition was poor, which may lead to more accurate and/or repeatable measurements. In some applications, the feedback may help users improve their data acquisition techniques, which may reduce the need to reacquire data.

In various examples where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, examples or processes described herein may be combined with one or more other examples, examples and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular example or group of examples. Thus, while the present system has been described in particular detail with reference to exemplary examples, it should also be appreciated that numerous modifications and alternative examples may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. An ultrasound imaging system configured to provide feedback on a quality of volume flow measurements, the system comprising:
   a user interface;
   a non-transitory computer readable medium encoded with instructions and configured to store power Doppler data for a plurality of Z-surfaces of a volume including a region of interest (ROI); and
   at least one processor in communication with the non-transitory computer readable medium configured to execute the instructions, wherein when executed, the instructions cause the at least one processor to:
   generate a histogram for individual ones of the plurality of Z-surfaces based, at least in part, on the power Doppler data, wherein the histogram has a first curve based on the power Doppler data from within the ROI and a second curve based on the power Doppler data from outside the ROI;
   calculate a signal-to-noise ratio (SNR) by subtracting in the logarithmic scale a peak of the second curve from a peak of the first curve for at least one of the plurality of Z-surfaces; and
   generate a quality factor based, at least in part, on the SNR;
   generate display data for a quality indicator based, at least in part, on the quality factor, wherein the quality indicator is indicative of the quality of the volume flow measurements,
   wherein the user interface is configured to display the quality indicator to a user based on the display data.

2. The ultrasound imaging system of claim 1, wherein the quality indicator comprises text indicating a value of the SNR.

3. The ultrasound imaging system of claim 1, wherein the quality indicator comprises a graphic including a color, wherein the color is based, at least in part, on a value of the SNR.

4. The ultrasound imaging system of claim 1, wherein the instructions further cause the at least one processor to:
   calculate the SNR for every Z-surface of the plurality of Z-surfaces; and
   calculate at least one of a median SNR or a mean SNR of the plurality of Z-surfaces, wherein the quality factor is based on at least one of the median SNR or the mean SNR.

5. The ultrasound imaging system of claim 1, wherein the instructions further cause the at least one processor to:
   calculate the SNR for every Z-surface of the plurality of Z-surfaces;
   calculate an interquartile range median (IQR/M) for each of a plurality of groups of Z-surfaces, wherein individual ones of the plurality of groups of Z-surfaces include a subset of the plurality of Z-surfaces;
   determine a group of the plurality of groups of Z-surfaces having a minimum IQR/M; and
   calculate at least one of a median SNR or a mean SNR of the group of the plurality of groups of Z-surfaces, wherein the quality factor is based on at least one of the median SNR or the mean SNR.

6. The ultrasound imaging system of claim 1, wherein the instructions further cause the at least one processor to:
   calculate the SNR for every Z-surface of the plurality of Z-surfaces;
   calculate a coefficient of variation (COV) for each group of a plurality of groups of Z-surfaces, where wherein individual ones of the plurality of groups of Z-surfaces include a subset of the plurality of Z-surfaces;
   determine a group of the plurality of groups of Z-surfaces having a minimum COV; and
   calculate at least one of a median SNR or a mean SNR of the group of the plurality of groups of Z-surfaces, wherein the quality factor is based on at least one of the median SNR or the mean SNR.

7. The ultrasound imaging system of claim 1, wherein the at least one Z-surface comprise a plurality of Z-surfaces proximate to a focus of an ultrasound beam used to collect the power Doppler data.

8. The ultrasound imaging system of claim 1, wherein the instructions further cause the at least one processor to:
generate at least one more quality factor, wherein the quality indicator is further based on the at least one more quality factor.

9. The ultrasound imaging system of claim 8, wherein the at least one more quality factor includes at least one of a presence of motion, a Doppler angle, a vessel size, a vessel depth, or a variance of the volume flow measurements within the ROI.

10. The ultrasound imaging system of claim 8, wherein the instructions further cause the at least one processor to:
generate second display data for a suggestion for improving the quality of the volume flow measurements, based at least in part, on the quality factor and the at least one more quality factor,
wherein the user interface is further configured to display the suggestion based on the second display data.

11. A method for providing feedback on a quality of volume flow measurements, the method comprising:
generating a histogram from power Doppler data for individual ones of a plurality of Z-surfaces in a volume of a subject, wherein the histogram has a first curve based on the power Doppler data from within a region of interest (ROI) and a second curve based on the power Doppler data from outside the ROI;
calculating a signal-to-noise ratio (SNR) by subtracting in the logarithmic scale a peak of the second curve from a peak of the first curve for at least one of the plurality of Z-surfaces; and
generating a quality factor based, at least in part, on the SNR;
generating display data for a quality indicator based, at least in part, on the quality factor, wherein the quality indicator is indicative of the quality of the volume flow measurements; and
displaying the quality indicator to a user based on the display data.

12. The method of claim 11, further comprising calculating at least one more quality factor, wherein the quality indicator is further based on the at least one more quality factor.

13. The method of claim 12, wherein the at least one more quality factor includes at least one of a presence of motion, a Doppler angle, a vessel size, a vessel depth, or a variance of the volume flow measurements within the ROI.

14. The method of claim 12, further comprising generating a suggestion for improving the quality of the volume flow measurements, based at least in part, on the quality factor and the at least one more quality factor.

15. The method of claim 14, wherein the suggestion comprises a graphic indicating at least one of a movement or a position of an ultrasound probe when a Doppler angle is determined to be greater than or equal to a threshold value.

16. The method of claim 14, wherein the suggestion comprises prompting the user to select a new ROI or adjust an imaging parameter when a ROI size is determined to be below or equal to a threshold value.

17. The method of claim 14, wherein the suggestion comprises prompting the user to select a new ROI or adjust an imaging parameter when a ROI depth is determined to be greater than or equal to a threshold value.

18. The method of claim 14, wherein the suggestion comprises prompting the user to hold a probe still or the subject to hold still when a presence of motion is detected.

19. The method of claim 11, wherein the quality indicator provides a qualitative indication of the quality of the volume flow measurements.

20. The method of claim 11, wherein the quality indicator provides a quantitative indication of the quality of the volume flow measurements.

* * * * *